United States Patent
Iida (10) Patent No.: US 6,994,709 B2
(45) Date of Patent: Feb. 7, 2006

(54) TREATMENT DEVICE FOR TISSUE FROM LIVING TISSUES

(75) Inventor: Koji Iida, Sagamihara (JP)

(73) Assignee: Olympus Corporation, (JP)

( * ) Notice: Subject to any disclaimer, the term of this patent is extended or adjusted under 35 U.S.C. 154(b) by 0 days.

(21) Appl. No.: 10/232,009

(22) Filed: Aug. 29, 2002

(65) Prior Publication Data

US 2003/0060816 A1    Mar. 27, 2003

(30) Foreign Application Priority Data

| Aug. 30, 2001 | (JP) | ............................ 2001-262132 |
| May 10, 2002 | (JP) | ............................ 2002-135601 |
| May 13, 2002 | (JP) | ............................ 2002-137104 |

(51) Int. Cl.
  *A61B 18/14*  (2006.01)
(52) U.S. Cl. ........................................ 606/49; 606/205
(58) Field of Classification Search ............ 606/49–52, 606/205–6
  See application file for complete search history.

(56) References Cited

U.S. PATENT DOCUMENTS

| 4,702,246 A | * | 10/1987 | Ellis et al. .................... 606/31 |
| 5,241,156 A | * | 8/1993 | Wallgren et al. ............. 219/233 |
| 5,403,312 A | * | 4/1995 | Yates et al. .................... 606/50 |
| 5,496,347 A | * | 3/1996 | Hashiguchi et al. ........ 606/205 |
| 5,514,134 A | | 5/1996 | Rydell et al. ................. 606/50 |
| 5,697,936 A | * | 12/1997 | Shipko et al. .............. 606/108 |
| 5,797,939 A | | 8/1998 | Yoon .......................... 606/167 |
| 6,334,860 B1 | * | 1/2002 | Dorn .......................... 606/48 |
| 6,464,701 B1 | * | 10/2002 | Hooven et al. ............... 606/50 |
| 6,929,645 B2 | * | 8/2005 | Battles et al. ................. 606/51 |

FOREIGN PATENT DOCUMENTS

| JP | 2002-136525 | 5/2002 |
| WO | 01/12090 | 2/2001 |

* cited by examiner

Primary Examiner—Roy D. Gibson
Assistant Examiner—Aaron Roane
(74) Attorney, Agent, or Firm—Ostrolenk, Faber, Gerb & Soffen, LLP (57) ABSTRACT

A pair of openable/closable jaws, an insertion section configured to support the pair of jaws, an operation section configured to open/close the pair of jaws, a heat generating element provided in a jaw, that generates heat by supply of electricity, electricity supply means configured to supply electricity to the heat generating element, and damage protecting means for protecting the electricity supply means from being damaged, are provided.

12 Claims, 12 Drawing Sheets

FIG. 12B

TREATMENT DEVICE FOR TISSUE FROM LIVING TISSUES

CROSS-REFERENCE TO RELATED APPLICATIONS

This application is based upon and claims the benefit of priority from the prior Japanese Patent Applications No. 2001-262132, filed Aug. 30, 2001; No. 2002-135601, filed May 10, 2002; and No. 2002-137104, filed May 13, 2002, the entire contents of all of which are incorporated herein by reference.

BACKGROUND OF THE INVENTION

1. Field of the Invention

The present invention relates to a therapeutic device for treating a tissue of a living tissues, that can coagulate and cut the tissue while holding it.

2. Description of the Related Art

Living tissue therapeutic devices that can coagulate and cut a tissue while holding it generally include a pair of holding members for holding a tissue of a living tissues. In these devices, a heat generator is provided on one or both sides of the holding members and the heat generator is turned on to generate heat while holding a tissue with the pair of the holding members so as to coagulate the tissue or cut the coagulated portion.

The tissue treatment devices of this type are used for various cases, such as hemostasis of a blood vessel contained in a living tissue, cauterization of a diseased portion or bleeding point on a surface layer of a living tissue, and blockage of the oviduct for the purpose of contraception. A living tissue therapeutic device is used to coagulate a tissue of a living tissues of the patient that needs to be treated, and then the coagulated living tissue can be cut with the therapeutic device.

For example, U.S. Pat. No. 5,514,134 discloses bipolar forceps used for a laparoscope, that open/close its jaws by means of a link mechanism. This document describes a structure in which two electrodes are electrically connected to the jaws that opens/closes by means of a driving shaft or a link mechanism.

U.S. Pat. No. 5,797,939 discloses surgical scissors equipped with a channel, but this channel is used for supplying water and suctioning.

Further, Jpn. Pat. Appln. KOKAI Publication No. 2002-136525 discloses a structure that includes a pair of openable/closable holding portions that can hold a tissue, in which a heater portion is provided in at least one of the holding portions, and a controllable heat generating means is provided independently from the heater portion.

However, according to the structure disclosed in U.S. Pat. No. 5,514,134 mentioned above, the supply of electricity is done via a driving shaft or a link mechanism. Here, since the two poles themselves must be insulated from each other while supplying electricity, the insulation structure is complicated. Meanwhile, U.S. Pat. No. 5,797,939 discloses surgical scissors equipped with a channel, but this document makes no mention of electricity supply means.

Further, Jpn. Pat. Appln. KOKAI Publication No. 2002-136525 discloses a structure in which a recess groove is made in its scissor structural portion in its longitudinal direction, and a lead line is inserted to the recess groove. Such a structure is very complicated, and cannot be employed as a treatment device for a tissue from a living tissues, used for an operated carried out using an endoscope, which includes a long and slender insertion portion.

BRIEF SUMMARY OF THE INVENTION

The object of the present invention is to provide a treatment device for a tissue from a living tissues, that can improve the durability of the electricity supply means and heat generating means, with a simple structure for supplying electricity to the heat generating means provided in a jaw.

According to an aspect of the present invention, there is provided a therapeutic device for treating a living tissue, comprising: a pair of openable/closable jaws at least one of which is movable; an insertion section configured to support the pair of jaws; an operation section configured to open/close the pair of jaws; heat generating means provided in a jaw, that generates heat by supply of electricity; electricity supply means configured to supply electricity to the heat generating means; and damage protecting means configured to protect the electricity supply means from being damaged.

Further, according to another aspect of the present invention, there is provided a therapeutic device for treating a living tissue, comprising: a pair of openable/closable jaws; an insertion section configured to support the pair of jaws; an operation section configured to open/close the pair of jaws; and heat generating means provided in a jaw, configured to generate heat by supply of electricity; soft, i.e., flexible electricity supply means configured to supply electricity to the heat generating means; and a space made in the insertion section, exclusively used for the electricity supply means to pierce therethrough.

Additional objects and advantages of the invention will be set forth in the description which follows, and in part will be obvious from the description, or may be leaned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will now be described in detail with reference to the accompanying drawings.

Figure 1A:
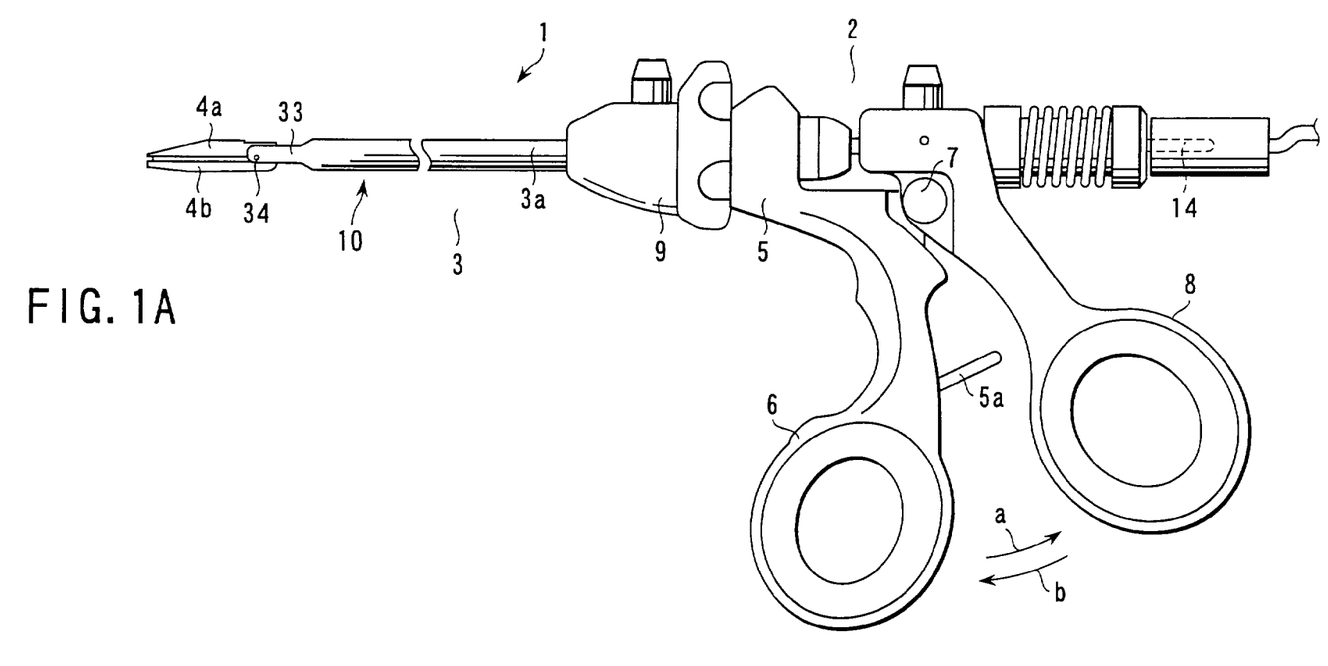
FIG. 1A is a side view of a thermal-coagulating cutting forceps according to the first embodiment of the present invention.

FIGS. 1A to 5F illustrates the first embodiment of the present invention. As can be seen in FIGS. 1A and 1B, thermal-coagulation cutting forceps 1 used for an operation using an endoscope, serving as a therapeutic device for a living tissue, include an operating portion 2, a slender insertion portion 3 provided for the operating portion 2 and first and second jaws 4a and 4b set in pair, that open/close against each other, provided in the distal end portion of the insertion portion 3.

Figure 1B:
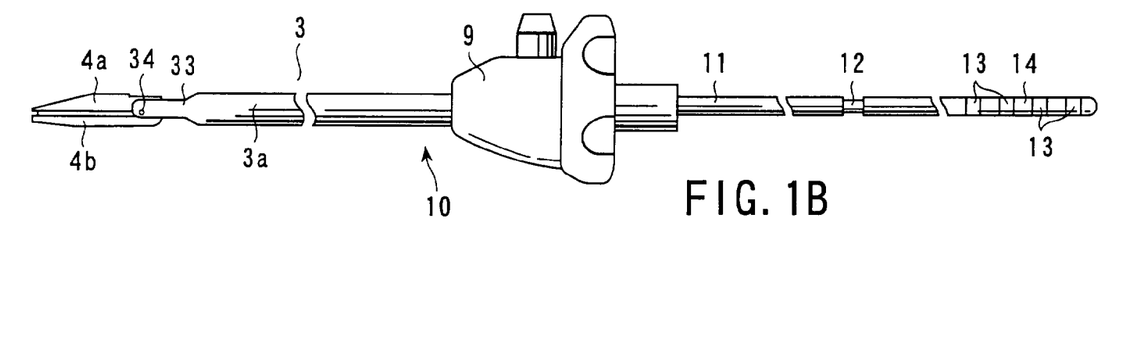
FIG. 1B is a side view of the embodiment shown in FIG. 1A, in a state in while its forceps unit is removed.

The insertion portion 2 includes a operating portion main body 5, a stationary handle 6 provided to be integral with the operating portion main body 5, and a movable handle 8 provided to be rotatable on the main body 5, around the pivotal shaft 7. The operating portion main body 5 is provided with a detachable forceps unit 10, such that the insertion portion 3 can be rotated with a rotation operating portion 9 around the axial center.

The insertion portion 3 is made of a small-diameter pipe 3a, and a drive shaft 11 that can move forwards and backwards in the axial direction is inserted to the insertion portion 3. The proximal end portion of the drive shaft 11 is connected to the movable handle 8. As the movable handle 8 is rotated in the direction indicated by an arrow a, the drive shaft moves forwards to open the first and second jaws 4a and 4b, whereas as the handle is rotated in the direction indicated by an arrow b, the drive shaft moves backwards to close the first and second jaws 4a and 4b. It should be noted that there is also provided a stopper 5a for regulating the rotation amount of the movable handle 8.

Further, an engagement portion 12 made of a notch is made on the proximal end portion side of the drive shaft 11. A plug 14 including a plurality of electrodes that are arranged to be apart from each other in the axial direction is provided on the further proximal side of the shaft, than the location of this engagement portion 12.

Figures 2A, 2B, 2C:
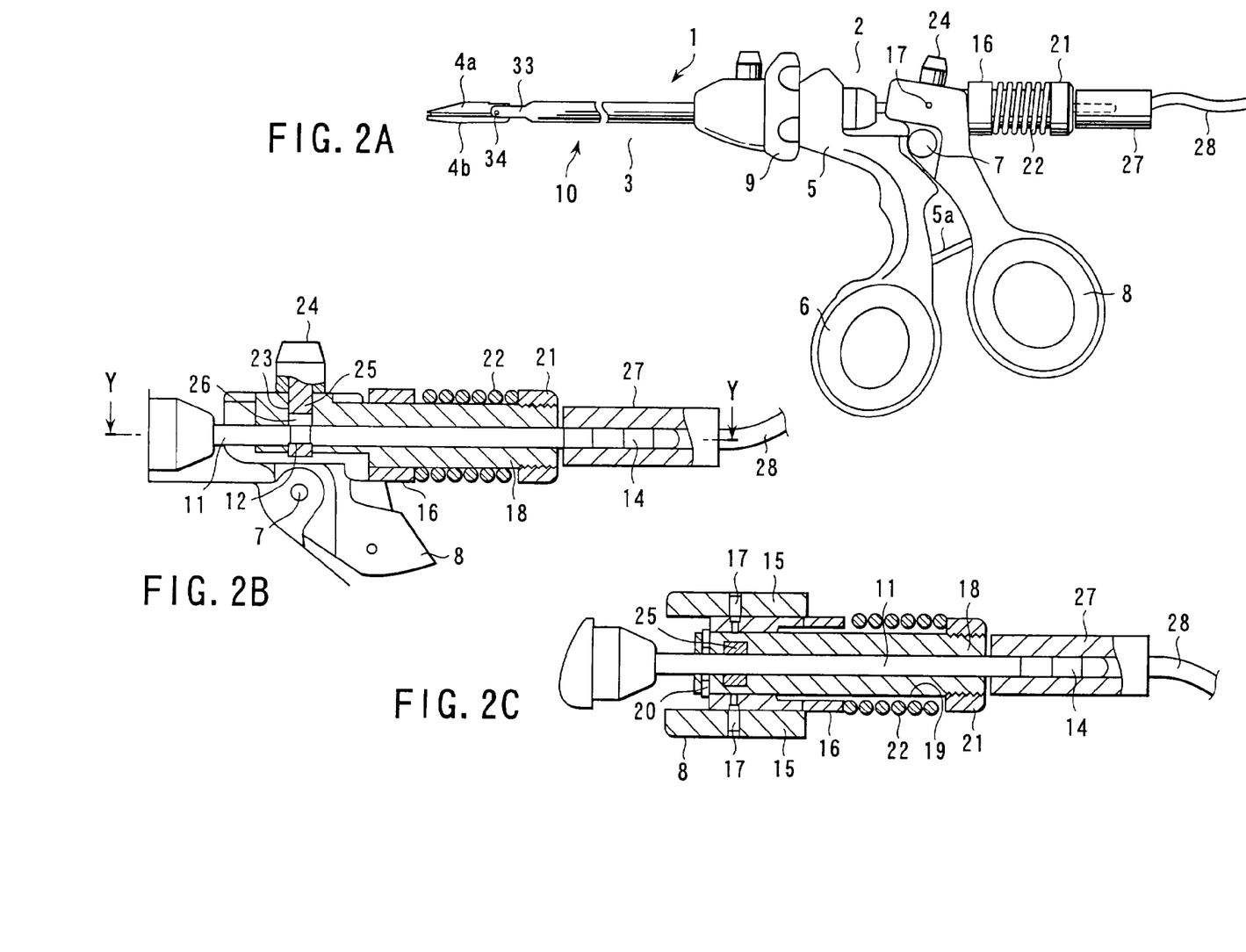
FIG. 2A is another side view of a thermal-coagulating cutting forceps according to the first embodiment.
FIG. 2B is a longitudinal section, viewed from side, of a handle over-load limiting mechanism of the forceps according to the same embodiment.
FIG. 2C is a cross sectional view of the forceps taken along the line Y—Y in FIG. 2B.

As can be seen in FIGS. 2A to 2C, the upper section of the movable handle 8 from the pivotal shaft 7 is provided with a support piece 15 that is formed to have a forked shape. Between these formed portions of the support piece 15, a slide member 16 is connected by means of a support pin 17. The slide member 16 has a cylindrical shape, in which a spring support member 18 is inserted slidably in the axial direction. A through hole 19 is made in the spring support member 18 in its axial direction, and the proximal end of the drive shaft 11 is pieced through the through hole 19.

A distal end side of the spring support member 18 has a lock pin 20 formed thereon, which abuts on the end surface of the slide member 16. A spring stopper member 21 is engaged to the proximal end side of the spring support member 18. Between the slide member 16 and the spring stopper member 21, a coil spring 22 is provided such as to fit in the spring support member 18.

With the above-described structure, when the movable handle 8 is rotated in the direction indicated by an arrow a as shown in FIG. 1A, the drive shaft 11 advances to open the first and second jaws 4a and 4b. When the movable handle 8 is rotated in the direction indicated by an arrow b, the drive shaft 11 retreats to close the first and second jaws 4a and 4b. If the operator further operates the movable handle 8 in the direction of the arrow b, the slide member 16 is moved to the proximal end side of the spring support member 18 via the support piece 15 of the movable handle 8, and thus the coil spring 22 is compressed. With this structure, even if an overload is applied to the movable handle 8, the coil springs 22 is compressed to regulate the overload, and therefore the overload does not act on the first and second jaws 4a and 4b. In this manner, damages to the first and second jaws 4a and 4b, as well as to the drive mechanisms that transmit the force thereto, can be prevented.

Further, a lock hole 23 is made in the spring support member 18 in the direction normally intersecting with the through hole 19. A lock member 25 is inserted to the lock hole 23, and the lock member is advanceable/retreatable by means of a detachable button 24 that is urged in its projecting direction. The lock member 25 has a lock hole 26 made therein, to be engaged with or disengaged from the engagement portion 12 of the drive shaft 11.

With the above-described structure, in a normal state, the lock member 25 is pulled up by the urging force of the detachable button 24 so that the lock hole 26 and the engagement portion 12 are engaged with each other. As the detachable button 24 is pulled down, the engagement between the lock hole 26 and the engagement portion 12 is released, and thus the drive shaft 11 can be extracted from the spring support member 18.

In the meantime, the plug 14 is detachably connected to a cable connector 27. The cable connector 27 is connected to a power source (not shown) via a cable 28.

The insertion portion 3 of the thermal-coagulating cutting forceps 1 has a structure as illustrated in FIGS. 3 to 5F. In the small-diameter pipe 3a which makes the insertion portion 3, a channel pipe 30 and a drive shaft channel 31 are provided in parallel with each other. The channel pipe 30 has a piercing space 32 serving as a piercing portion through which a coaxial cable, which will be later described, is put. Through the drive shaft channel 31, the drive shaft 11 is put to be advanceable or retreatable.

Figure 3:
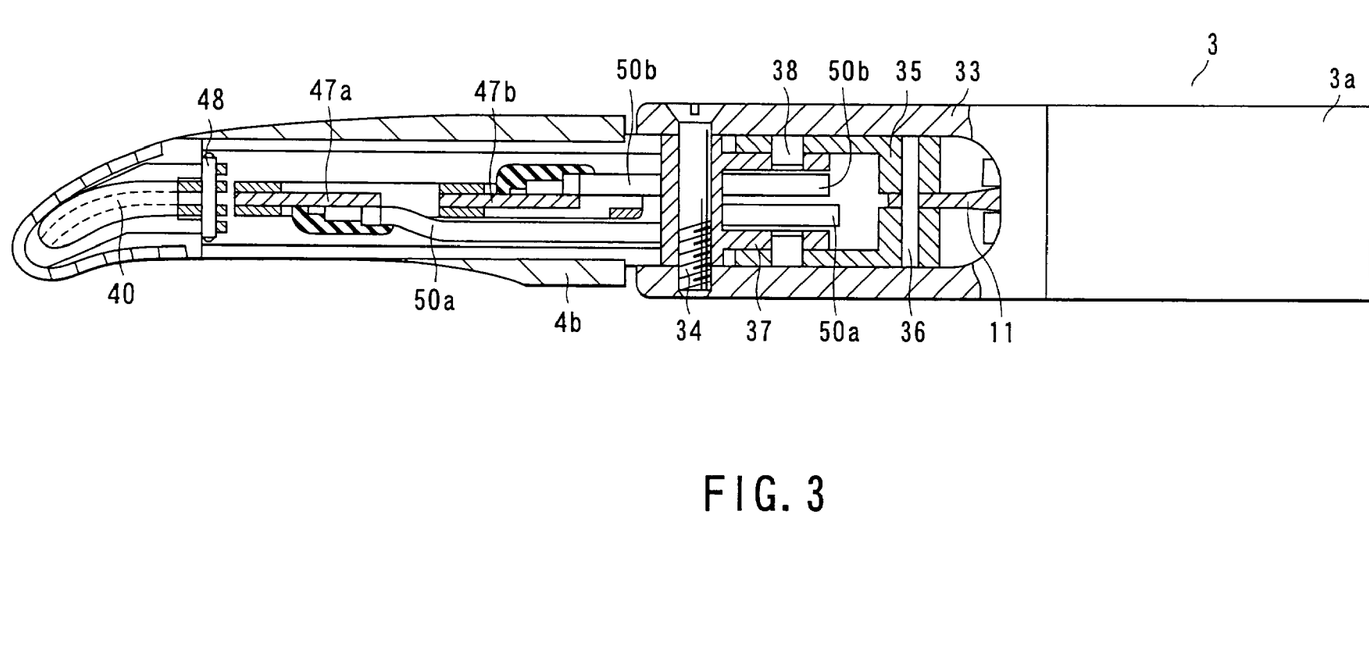
FIG. 3 is a longitudinal section, viewed from above, of a distal end portion of an insertion portion of the thermal-coagulating cutting forceps according to the first embodiment.

At a distal end portion of the insertion portion 3, a support member 33 is provided to project out in a forward direction. A basal portion 33a of the support member is fixed to the distal end of the small-diameter pipe 3a. At the distal end portion of the support member 33, a pivot pin 34 is provided to pierce therethrough in its lateral direction.

Figure 4A:
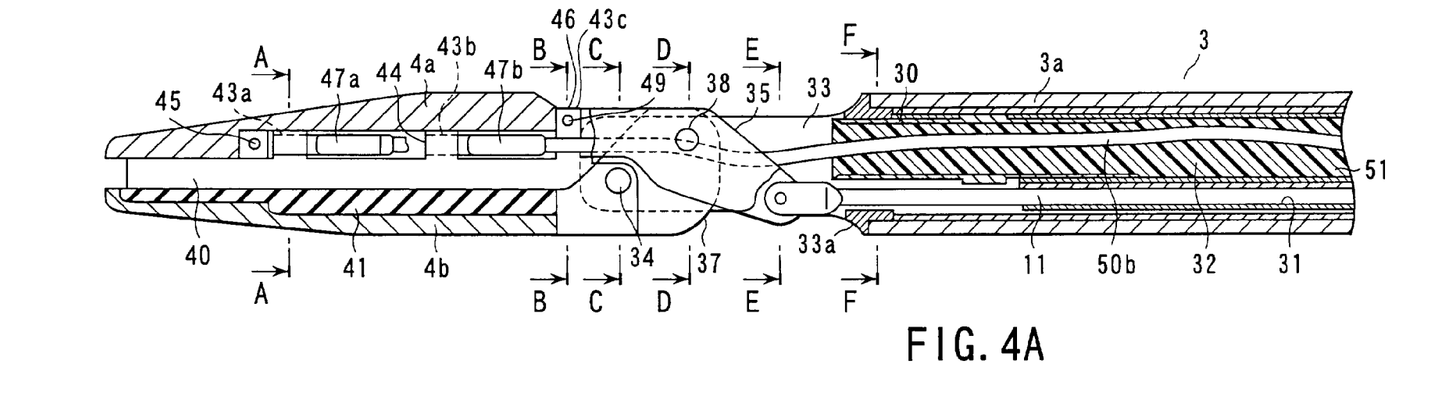
FIG. 4A is a longitudinal section, viewed from side, of the distal end portion of the insertion portion of the thermal-coagulating cutting forceps according to the first embodiment, in a state where the jaws are closed.
Figure 4B:
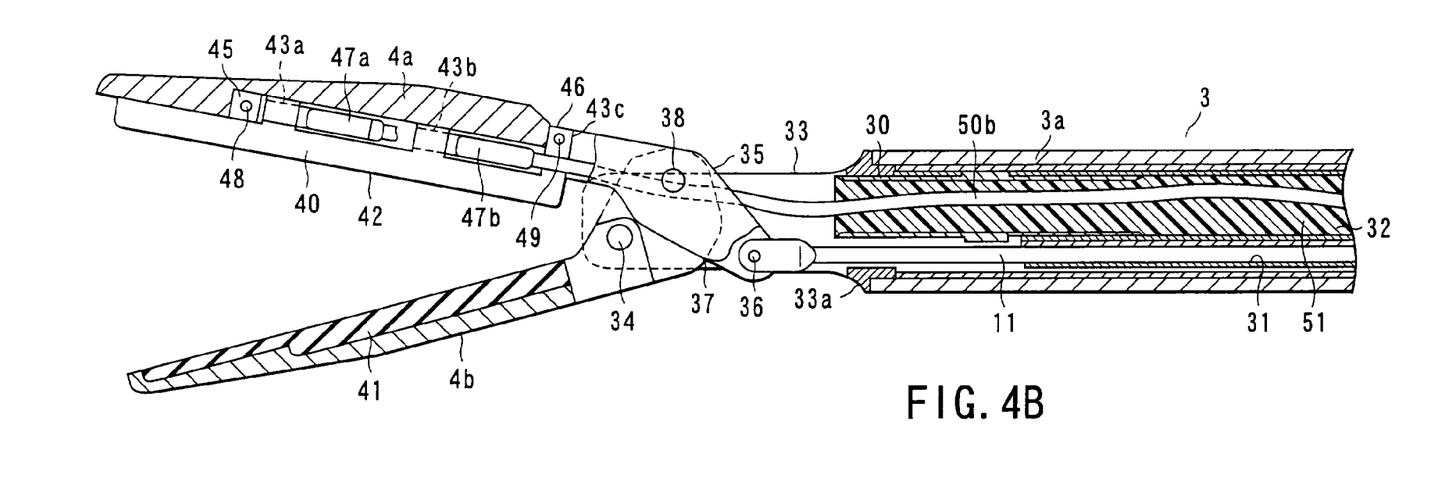
FIG. 4B is a longitudinal section, viewed from side, of the forceps according to the first embodiment, in a state where the jaws are opened.
Figure 5A:
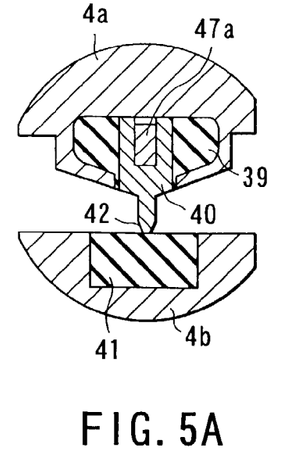
FIG. 5A is a cross sectional view of the forceps taken along the line A—A in FIG. 4A.
Figure 5B:
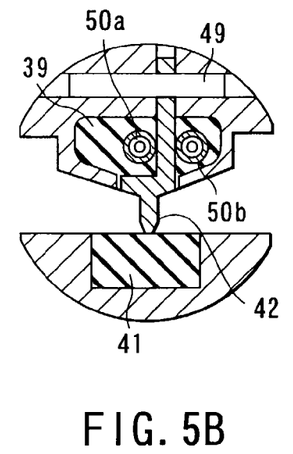
FIG. 5B is a cross sectional view of the forceps taken along the line B—B in FIG. 4A.
Figure 5C:
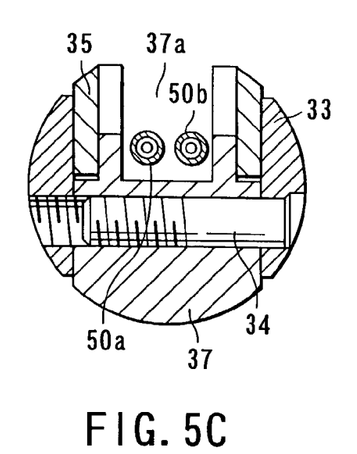
FIG. 5C is a cross sectional view of the forceps taken along the line C—C in FIG. 4A.
Figure 5D:
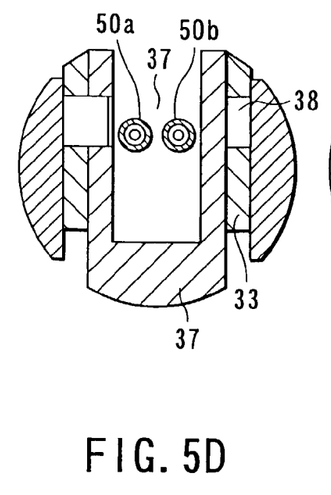
FIG. 5D is a cross sectional view of the forceps taken along the line D—D in FIG. 4A.
Figures 5E, 5F:
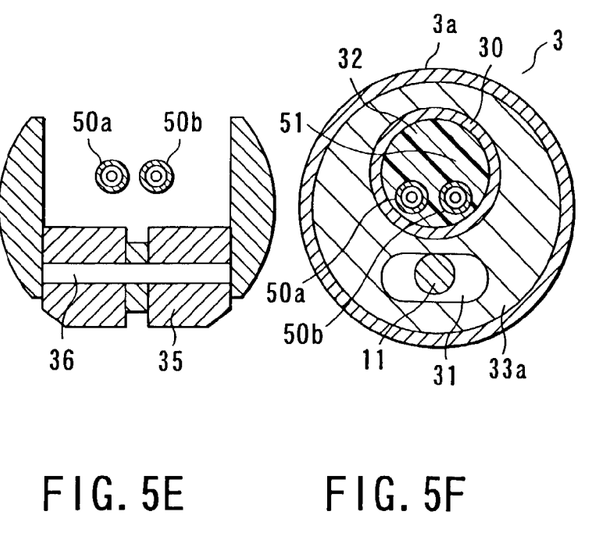
FIG. 5E is a cross sectional view of the forceps taken along the line E—E in FIG. 4A.
FIG. 5F is a cross sectional view of the forceps taken along the line F—F in FIG. 4A.

The second jaw 4b is rotatably pivoted on the pivot pin 34. A proximal end arm portion 35 of the first jaw 4a is formed to have a fork shape, and the fork-shaped section is rotatably coupled to the drive shaft 11 via a coupling pin 36. A proximal end arm portion 37 of the second jaw 4b is formed to have a fork shape, and the fork-shaped section is rotatably connected to the proximal end arm portion 35 of the first jaw 4a by means of a connection pin 38. Thus, with the forked shape, a coaxial cable insertion space 37a serving as an insertion portion, which will be later described, is formed in the proximal end arm portion 37 of the second jaw 4b.

With the above-described structure, when the drive shaft 11 advances forwards, the first jaw 4a rotates upwards as it is pivoted around the connection pin 38, whereas the second jaw 4b rotates downwards as it is pivoted around the pivot pin 34. In this manner, the first and second jaws 4a and 4b are opened. On the contrary, when the drive shaft 11 moves backwards, the first jaw 4a rotates downwards as it is pivoted around the connection pin 38, whereas the second jaw 4b rotates upwards as it is pivoted around the pivot pin 34. In this manner, the first and second jaws 4a and 4b are closed.

In the meantime, the first and second jaws 4a and 4b are formed such that their distal end portions are curved to the left side as they are seen from top, and with the curved shape, a tissue can be easily separated off. Further, a holding surface of the first jaw 4a, that is, the surface that is brought into contact with a living tissue, is provided with a thin heat generating plate 40 made of, for example, copper, which has an excellent heat conductivity. On the other hand, a holding surface of the second jaw 4b is provided with a soft member 41. The heat generating plate 40 and the soft member 41 are curved to follow the curved shape o the first and second jaws 4a and 4b. In the first jaw 4a, cavity portions are made on both sides of the heat generating plate 40, and these cavity portions are filled with a filler material 39 such as a heat insulator.

The heat generating plate 40 is a rectangular metal plate placed along the longitudinal direction of the first jaw 4a, and a blade portion 42 having such a tapered shape that the thickness decreases towards its distal end, is provided at the lower side portion of the plate over its longitudinal direction.

At the upper side portion of the heat generating plate 40, a plurality of, in this embodiment, three projection pieces 43a, 43b and 43c are arranged in the longitudinal direction at predetermined intervals, such as to project upwards. A slot is made in each of the projection pieces 43a, 43b and 43c in its vertical direction, and each slot makes a heat coupling portion 44.

The projection piece 43a that is located on the distal end side of the first jaw 4a has a through hole 45 pierced through in its lateral direction. The projection piece 43c that is located on the proximal end side of the first jaw 4a has a fixation plate 46 that is made integral with the projection piece and projects upwards further than the other projection pieces 43a and 43b.

In the heat coupling portions 44 made between the projection pieces 43a, 43b and 43c, heat generating members 47a and 47b serving as heat generating means and made of, for example, a thin-film heat resistance element are fixed respectively by a heat coupling way in the state where parts of the heat generating members are located within the respective slots. The heat generating members 47a and 47b are arranged at equal intervals so as to make the temperature distribution uniform.

In the distal end side of the first jaw 4a, both end portions of a fixation pin 48 provided to pierce the through hole 45 in its lateral direction are fixed, whereas in its proximal end side, the fixation plate 46 is fixed by a fixation pin 49.

Coaxial cables 50a and 50b are connected respectively and independently to the heat generating members 47a and 47b. The coaxial cables 50a and 50b have such a structure that at least two pairs of electroconductive cables are covered by a protection member made of a coating material. The protection member here is designed to prevent the disconnection of the cables, and to secure the insulation of the cables. The present invention is not limited to the coaxial cables, but single-wire cables may be employed. Here, a single-wire cable may be of such a structure that an electroconductive cable is protected by a protection member made of a coating material, such as a flexible tube.

The coaxial cables 50a and 50b pass through the coaxial cable insertion space 37a that is made by the forked shape of the proximal end arm portion 37 of the second jaw 4b, and are pierced through the piercing space 32 in the insertion portion 3. Then, the coaxial cables 50a and 50b are connected to the electrodes 13. The front ends of the coaxial cables 50a and 50b are held by the filler material 39. Further, the piercing space 32 of the insertion portion 3 is filled with a filler material 51 so as to hold the coaxial cables 50a and 50b.

Next, the operation of the thermal-coagulating cutting forceps 1 having the above-described structure will now be described.

First, the first and second jaws 4a and 4b are closed and are plugged into a part of a living tissue that is to be treated, such as a blood vessel, (not shown). Then, the movable handle 8 of the operation member 2 is rotated in the direction indicated by an arrow a around the pivotal shaft 7, and thus the drive shaft 11 is moved forwards. As the drive shaft 11 advances, the first jaw 4a rotates upwards around the connection pin 38, and the second jaw 4b rotates downwards around the pivotal pin 34. In this manner, the first and second jaws are opened, and thus the part to be treated such as a blood vessel can be separated from the other part of the living tissue, and exposed.

Subsequently, the separated part, that is, here, a blood vessel, is placed between the first and second jaws 4a and 4b. Then, the movable handle 8 of the operation member 2 is rotated in the direction indicated by an arrow b around the pivotal shaft 7, and thus the drive shaft 11 is moved backwards. As the drive shaft 11 retreats, the first jaw 4a rotates downwards around the connection pin 38, and the second jaw 4b rotates upwards around the pivotal pin 34. In this manner, the first and second jaws are closed, and thus the blood vessel is held with a pressure force that is appropriate for the required coagulation treatment.

While the part is being held as described above, an electrical current is supplied to the heat generating members 47a and 47b provided in the heat generating plate 40 of the first jaw 4a from the power source via the connector cable 28 as well as the connector 27 and the coaxial cables 50a and 50b. Due to the electric resistance that occurs during the supply of the current, the heat generating members 47a and 47b generate heat, and thus the part to be treated of the living tissue, such as a blood vessel, that are in contact with the surface of the heat generating plate 40 is coagulated and cut.

Here, the first jaw 4a is provided with two heat generating members 47a and 47b, and the coaxial cables 50a and 50b are respectively and independently connected to the heat generating members 47a and 47b, in order to connect the members to the power source. With this structure, each of the heat generating members 47a and 47b can be controlled independently to a set temperature.

It should be noted that the coaxial cables 50a and 50b are protected by the protection member made of the coating material, and housed in the insertion space 37a; therefore, with this structure, a damage to the cable while the apparatus is in use, or the breakage of the cable while the apparatus is being washed, does not easily occur. Further, the front and rear ends of the coaxial cables 50a and 50b are fixed with the filler material 39, and with this structure, an excessive force does not propagate to the heat generating members 47a and 47b, thus making it possible to prevent a damage to these members 47a and 47b.

More specifically, in the case where the section of the heat generating plate 40 which is in contact with the living tissue, for example, the distal end side of the heat generating plate 40 lowers its calorific value, thereby decreasing the temperature at the section, the resistance value of the heat generating member 47a provided on the distal end side is detected, and the output to the heat generating member 47a is increased. On the other hand, in the case where the section, which is not in contact with the living tissue, for example, the proximal end side of the heat generating plate 40, raises its calorific value, the output to the heat generating member 47b on the proximal end side is decreased. With the above-described operations, an uneven temperature distribution of the heat generating plate 40 can be prevented, and the coagulation and cutting can be quickly and accurately performed.

Further, the heat generating plate 40 is formed to be curved in accordance with the curved shape of the first jaw 4a. With this structure, if a straight heat generating plate 40 is assembled with the curved first jaw 4a, the first jaw 4a is widened in its width direction, thereby making it thick as a whole. In order to avoid this, the heat generating plate 40 is curved to follow the curvy shape of the first jaw 4a, thereby making it possible to achieve a slender structure as a whole.

The heat generating plate 40 should preferably be made of a material having a high heat conductivity such as copper, silver or tungsten, and the heat generating members 47a and 47b may be thin film resistance heating elements, ceramic heaters, cartridge heaters, PTC heaters or the like.

Examples of the material for the soft member 14 are rubbers (such as silicon rubber, fluorine rubber, ethylenepropylene rubber and butyl rubber), gels (including a silicon-based α-gel) and Teflon (registered tradename).

Figures 6A, 6B:
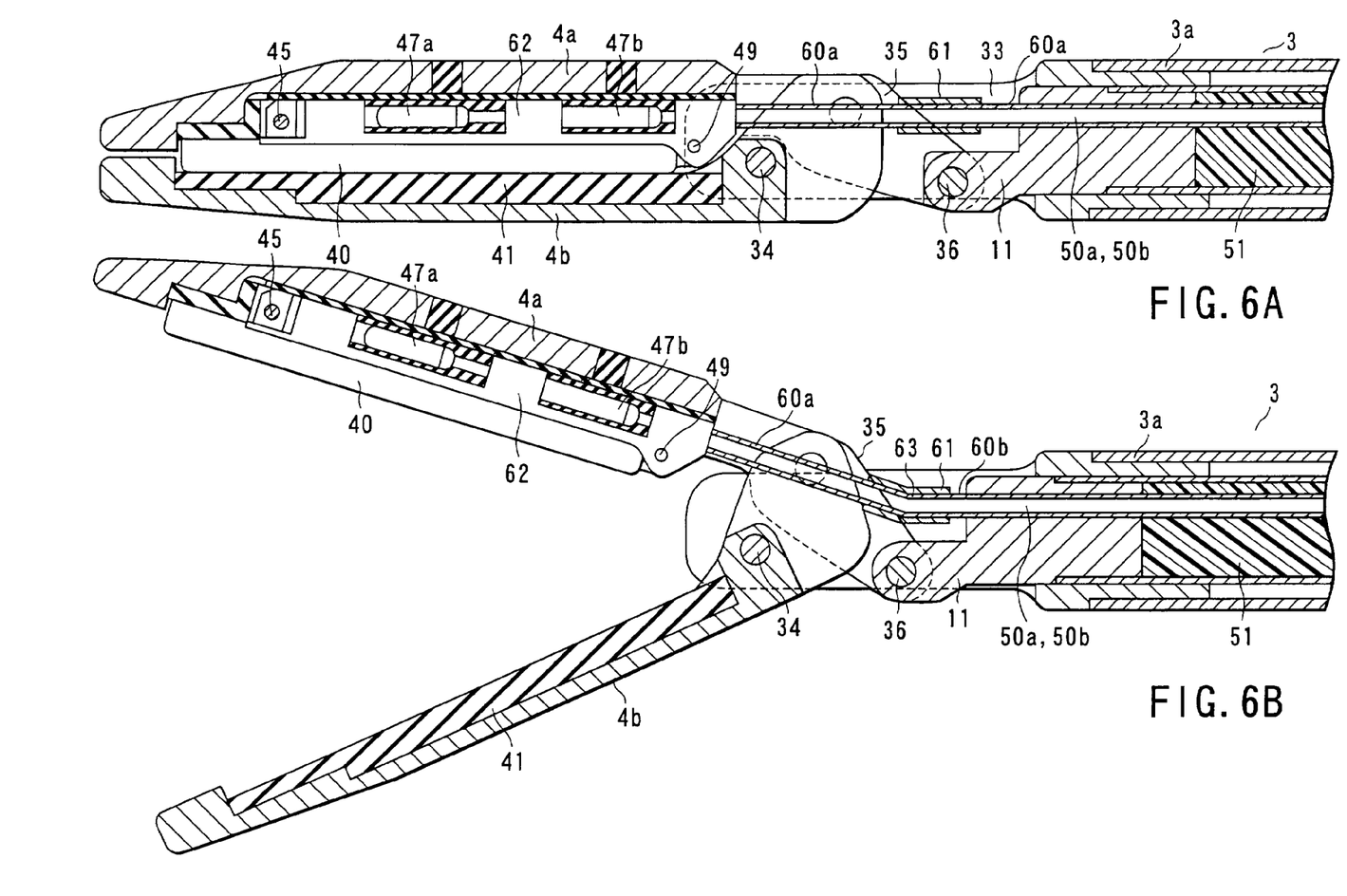
FIG. 6A is a longitudinal section, viewed from side, of the forceps according to the second embodiment, in a state where the jaws are closed.
FIG. 6B is a longitudinal section, viewed from side, of the forceps in a state where the jaws are closed.

FIGS. 6A and 6B illustrate the second embodiment of the present invention. Here, the same structural elements as those of the first embodiment will be designated by the same reference numerals, and the explanations for those elements will not be repeated.

As can be seen in FIGS. 6A and 6B, the coaxial cables 50a and 50b used for supplying electricity to the heat generating members 47a and 47b are pierced through hard pipes 60a and 60b, respectively. The pipes 60a and 60b are connected to each other by means of a flexible connection member 61. Examples of the material for the connection member 61 are a resin such as fluorine resin, a rubber such as silicon rubber, Teflon (registered name), a coil-like metal spring, as well as a composite material of a rubber/resin and a coil spring. The outer diameter of the coaxial cables 50a and 50b should preferably be as small as possible as compared to the inner diameter of the pipes 60a and 60b, in order to suppress damages that usually occurs in a bent portion 63. This embodiment exhibits such an advantage that the fixation of the coaxial cables 50a and 50b can be more secured.

It should be noted here that the electricity supply means is not limited to the coaxial cables 50a and 50b, but it may be a single-wire cable. In other wards, it may be of a type obtained by protecting a conductive cable with a protecting member made of a covering material, such as a flexible tube.

Further, the front end portion of the pipe 60a is connected to a part of a heat insulating material 62 provided outside the heat generating plate 40 in the first jaw 4a, and the rear end portion of the pipe 60b is connected to the drive shaft 11. In the case of the protecting member such as a flexible tube that covers the conductive cable, its front end portion is fixed to the first jaw 4a as well.

Figures 7A, 7B:
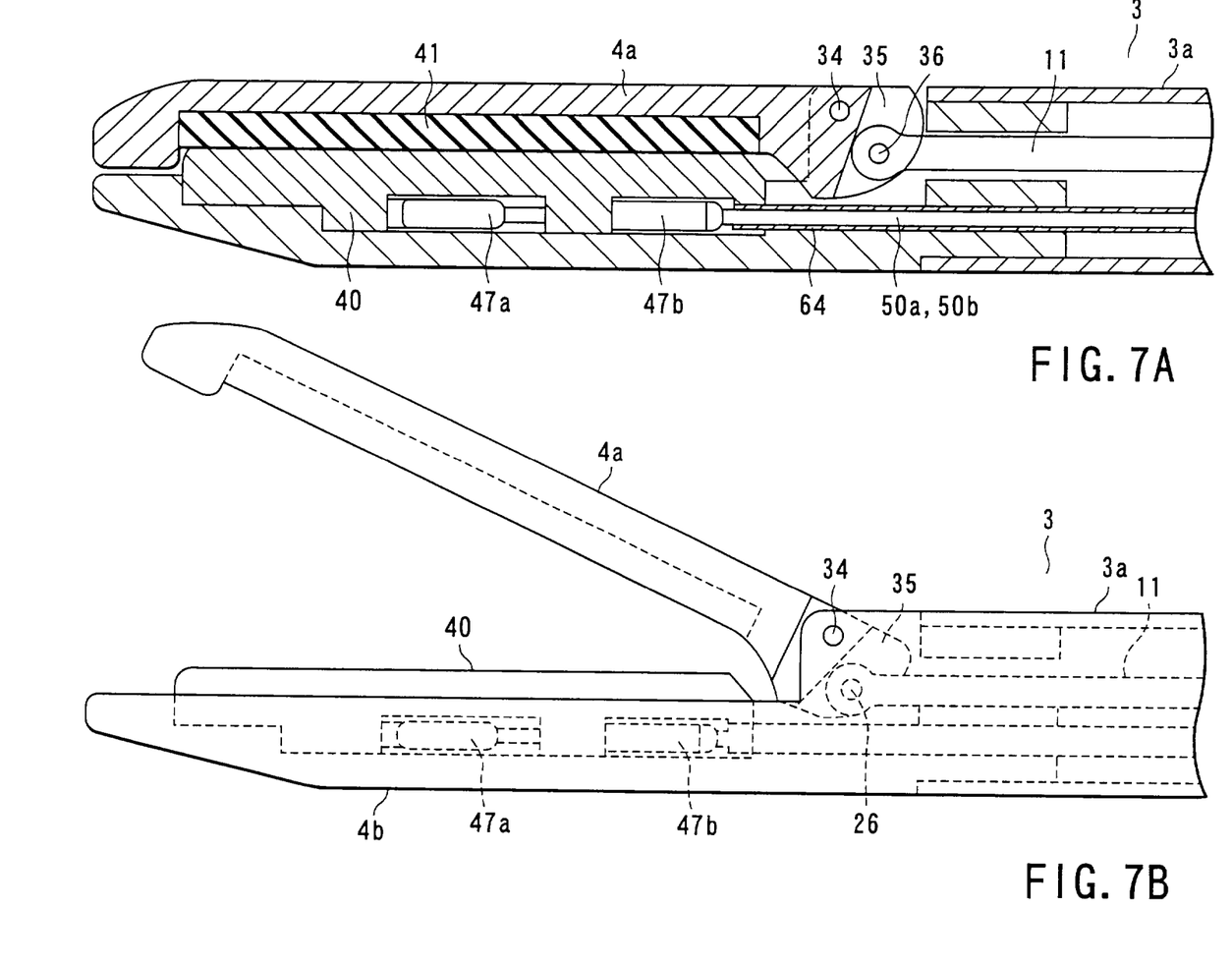
FIG. 7A is a longitudinal section, viewed from side, of the forceps according to the third embodiment, in a state where the jaws are closed.
FIG. 7B is a longitudinal section, viewed from side, of the forceps in a state where the jaws are closed.

FIGS. 7A and 7B illustrate the second embodiment of the present invention. Here, the same structural elements as those of the first embodiment will be designated by the same reference numerals, and the explanations for those elements will not be repeated.

As can be seen in FIGS. 7A and 7B, a stationary jaw 4a is provided at a distal end of the insertion portion 3, and a movable jaw 4b is supported to be openable/closable on the stationary jaw 4a. The heat generating plate 40 is provided on the stationary jaw 4a, and the soft member 41 is provided on the movable jaw 4b. A pipe 64 is disposed inside the stationary jaw 4a, and the coaxial cables 50a and 50b used to supply electricity to the heat generating members 47a and 47b are housed in the pipe 64.

According to this embodiment, parts such as heat generating members and electricity supplying means are fixed to the stationary jaw, and therefore the overall structure can be further simplified. It should be noted that when the above-described structure employed in the thermal coagulation forceps or thermal cutting forceps, the same advantage described as above can be obtained.

Figure 8A:
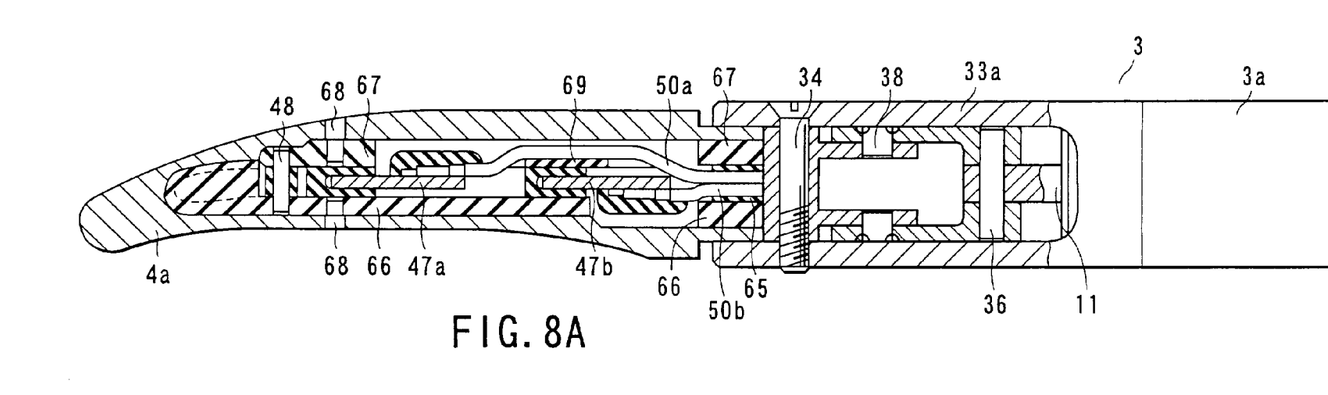
FIG. 8A is a longitudinal section, viewed from above, of an insertion portion of the thermal-coagulating cutting forceps according to the fourth embodiment of the present invention, taken along the line G—G in FIG. 8B.
Figure 8B:
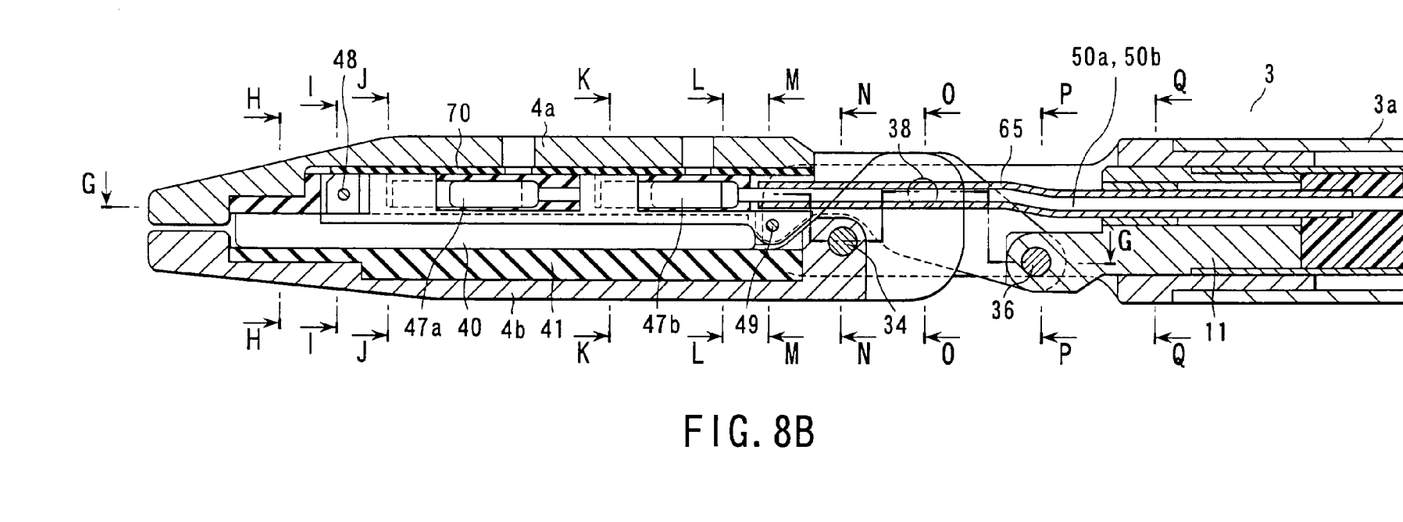
FIG. 8B is a longitudinal section, viewed from above, of the thermal-coagulating cutting forceps according to the fourth embodiment.
Figure 9A:
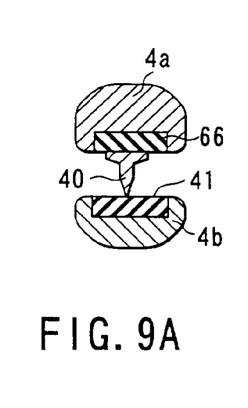
FIG. 9A is a cross sectional view of the forceps according to the fourth embodiment, taken along the line H—H in FIG. 8B.
Figure 9B:
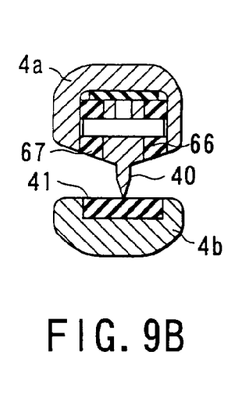
FIG. 9B is a cross sectional view of the forceps according to the fourth embodiment, taken along the line I—I in FIG. 8B.
Figure 9C:
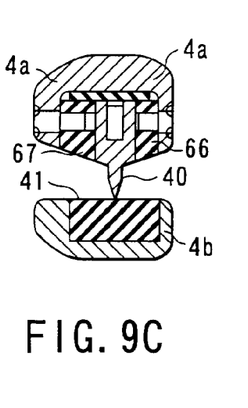
FIG. 9C is a cross sectional view of the forceps according to the fourth embodiment, taken along the line J—J in FIG. 8B.
Figure 9D:
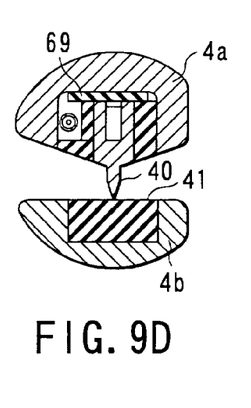
FIG. 9D is a cross sectional view of the forceps according to the fourth embodiment, taken along the line K—K in FIG. 8B.
Figure 9E:
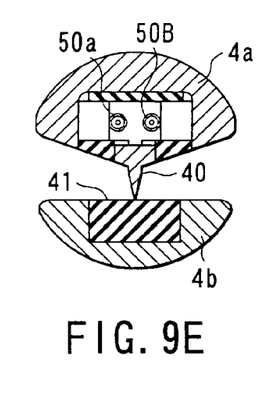
FIG. 9E is a cross sectional view of the forceps according to the fourth embodiment, taken along the line L—L in FIG. 8B.
Figure 9F:
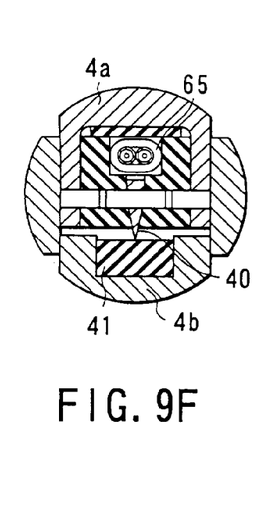
FIG. 9F is a cross sectional view of the forceps according to the fourth embodiment, taken along the line M—M in FIG. 8B.
Figure 9G:
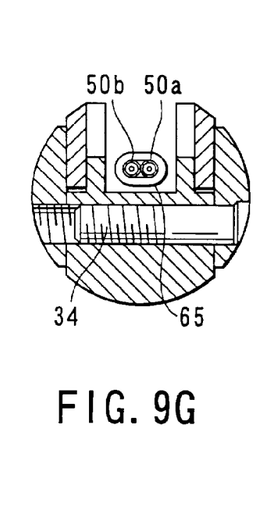
FIG. 9G is a cross sectional view of the forceps according to the fourth embodiment, taken along the line N—N in FIG. 8B.
Figure 9H:
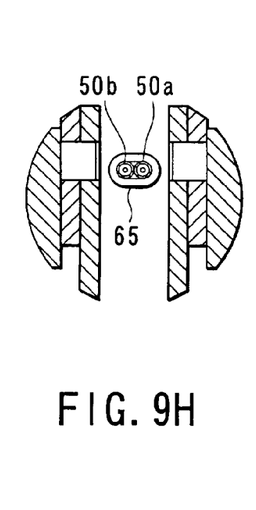
FIG. 9H is a cross sectional view of the forceps according to the fourth embodiment, taken along the line O—O in FIG. 8B.
Figure 9I:
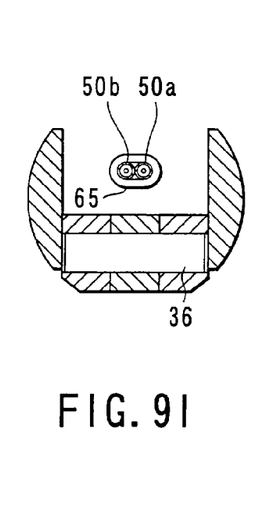
FIG. 9I is a cross sectional view of the forceps according to the fourth embodiment, taken along the line P—P in FIG. 8B.
Figure 9J:
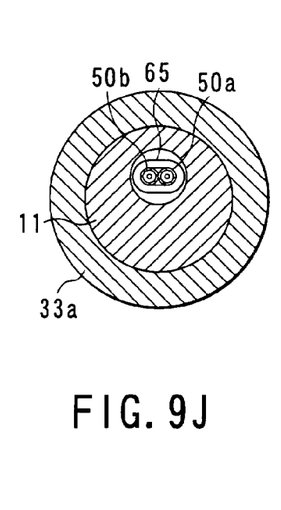
FIG. 9J is a cross sectional view of the forceps according to the fourth embodiment, taken along the line Q—Q in FIG. 8B.

FIGS. 8A and 9J illustrate the fourth embodiment of the thermal coagulation and cutting forceps according to the present invention. Here, the same structural elements as those of the first embodiment will be designated by the same reference numerals, and the explanations for those elements will not be repeated.

As can be seen in FIGS. 8A and 9J, the coaxial cables 50a and 50b used as electricity supplying means are pierced inside a resin tube 65. The distal end portion of the pipe 65 is adhered between heat insulating members 66 and 67. Further, the outer diameter of the resin tube 65 is larger than the gap between the heat insulating members 66 and 67, and therefore the tube is pushed into the gap while assembling, thereby creating a so-called calked state.

Further, the rear end portion of the resin tube 65 is adhered to the drive shaft 11. The outer diameter of the coaxial cables 50a and 50b is made smaller as compared to the inner diameter of the pipe 65, and thus it is possible to easily follow the bending of the resin tube 65. It should be noted here that the resin tube may be a thermal contraction tube.

The coaxial cables 50a and 50b serving as the electricity supplying means are formed integrally with in the drive shaft 11. The coaxial cables 50a and 50b are arranged such that one is located on a left side and the other on a right side with respect to the center axis that defines the center of the insertion portion 3. The heat insulating members 66 and 67 are fixed to one jaw, that is the jaw 4a, via fixation pins 68 and 49. Further, heat insulating members 69 and 70 are provided around the heat generating members 47a and 47b.

According to this embodiment, coaxial cables serving as electricity supplying means are provided within the drive shaft, and therefore the size of the drive shaft can be increased, thus making it possible to further strengthen the shaft. Further, with such an arrangement that the coaxial cables are distributed to left and right sides, the size of the jaws can be reduced.

Figure 10A:
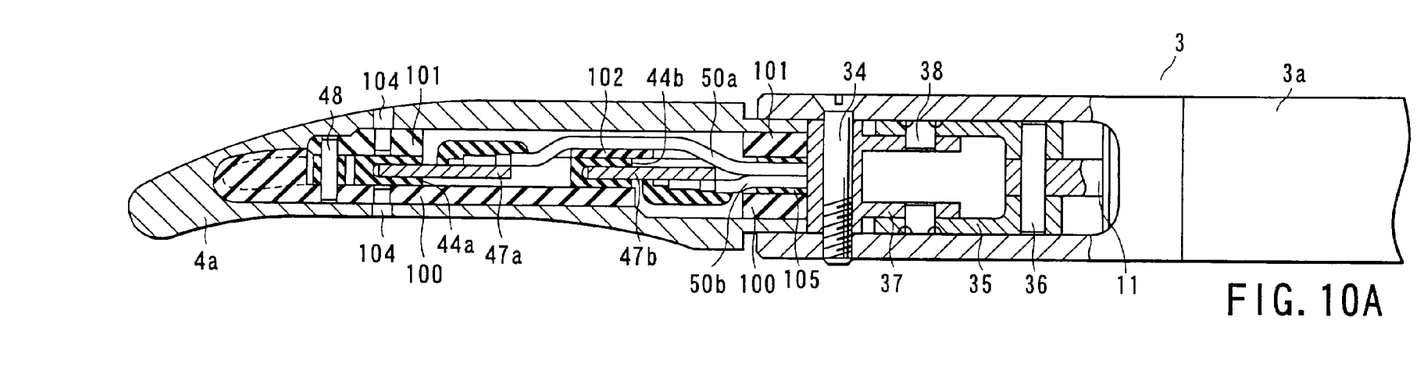
FIG. 10A is a longitudinal section, viewed from above, of an insertion portion of the thermal-coagulating cutting forceps according to the fifth embodiment of the present invention, taken along the line K'—K' in FIG. 10B.
Figure 10B:
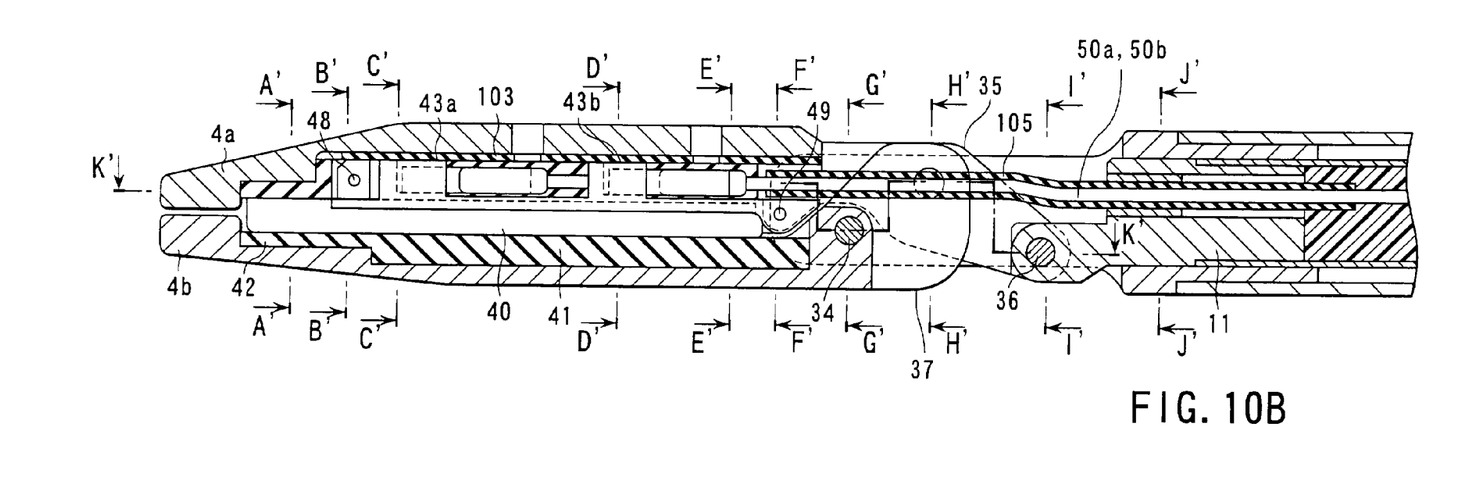
FIG. 10B is a longitudinal section, viewed from side, of the thermal-coagulating cutting forceps according to the fifth embodiment.
Figure 11A:
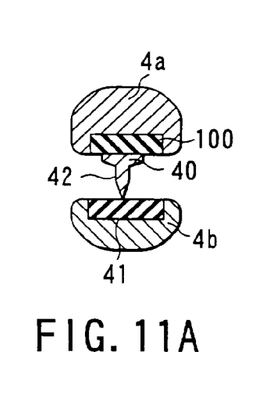
FIG. 11A is a cross sectional view of the forceps according to the fifth embodiment, taken along the line A'—A' in FIG. 10B.
Figure 11B:
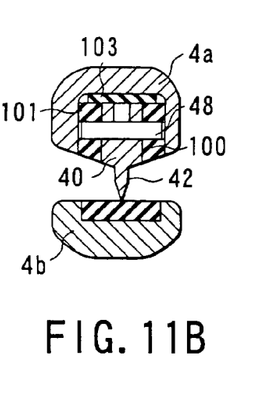
FIG. 11B is a cross sectional view of the forceps according to the fifth embodiment, taken along the line B'—B' in FIG. 10B.
Figure 11C:
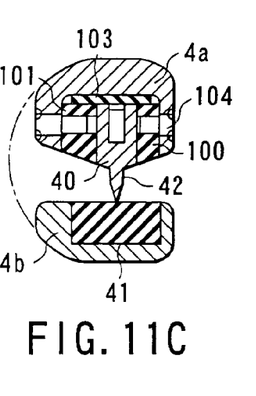
FIG. 11C is a cross sectional view of the forceps according to the fifth embodiment, taken along the line C'—C' in FIG. 10B.
Figure 11D:
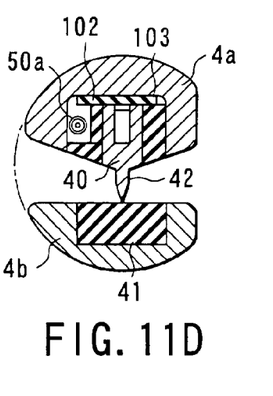
FIG. 11D is a cross sectional view of the forceps according to the fifth embodiment, taken along the line D'—D' in FIG. 10B.
Figure 11E:
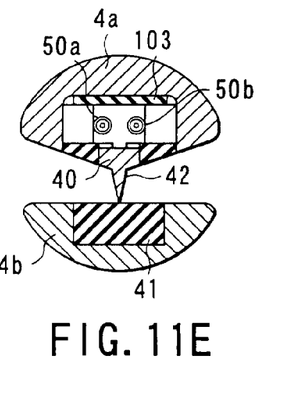
FIG. 11E is a cross sectional view of the forceps according to the fifth embodiment, taken along the line E'—E' in FIG. 10B.
Figure 11F:
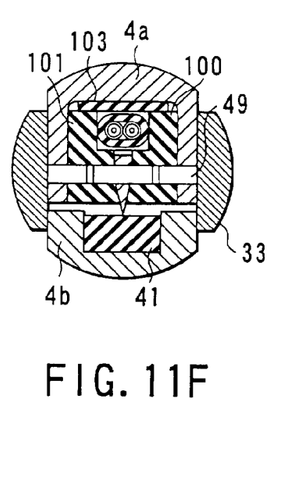
FIG. 11F is a cross sectional view of the forceps according to the fifth embodiment, taken along the line F'—F' in FIG. 10B.
Figure 11G:
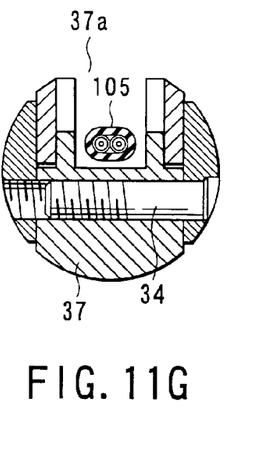
FIG. 11G is a cross sectional view of the forceps according to the fifth embodiment, taken along the line G'—G' in FIG. 10B.
Figure 11H:
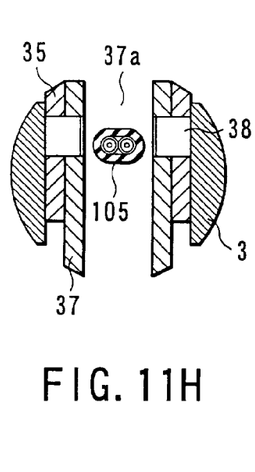
FIG. 11H is a cross sectional view of the forceps according to the fifth embodiment, taken along the line H'—H' in FIG. 10B.
Figure 11I:
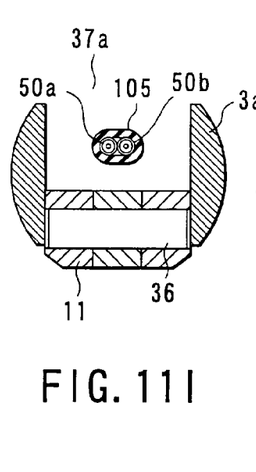
FIG. 11I is a cross sectional view of the forceps according to the fifth embodiment, taken along the line I'—I' in FIG. 10B.
Figure 11J:
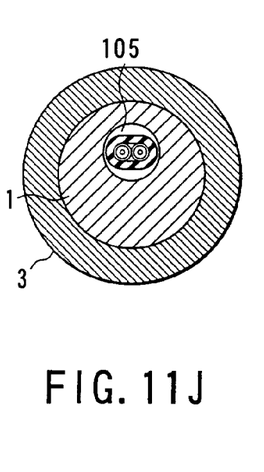
FIG. 11J is a cross sectional view of the forceps according to the fifth embodiment, taken along the line J'—J' in FIG. 10B.

FIGS. 10A and 11J illustrate the fifth embodiment of the thermal coagulation and cutting forceps according to the present invention. Here, the same structural elements as those of the first embodiment will be designated by the same reference numerals, and the explanations for those elements will not be repeated.

In the first jaws 4a, cavity portions are formed on both sides and upper side of the heat generating plate 40, and the first to fourth heat insulating members 100, 101, 102 and 103 are filled into these cavity portions. These heat insulating members 100, 101, 102 and 103 are disposed to be adjacent to the heat generating means within the first jaw 4a.

The first heat generating member 100 is provided to extend from the distal end side of the jaw 4a to the proximal end side along one side of the heat generating plate 40, and the second heat generating member 101 is provided to extend to the proximal end side along the other side of the heat generating plate 40. The third heat insulating member 102 is disposed between one of the coaxial cables, that is, cable 50a, and the projecting piece 43b of the heat generating plate. Further, the fourth heat insulating member 103 is provided to expend along the upper side of the heat generating plate 40 in its longitudinal direction.

The projecting piece 43a of the first jaw 4a is fixed to the heat insulating members 100 and 101 arranged on both side of the projecting piece 43a by means of the fixation pins 48 and 104 that pierce through in the lateral direction. The proximal end portion of the heat generating plate 40 is fixed to the heat insulating members 100 and 101 arranged on both side of the heat generating plate 40 by means of the fixation pins 49 that pierces through in the lateral direction.

The first and second heat insulating members 100 and 101 are made to be relatively thick, whereas the third and fourth heat insulating members 102 and 103 can be made thin in accordance with the size of the first jaw 4a. With this structure, even in the case of the jaws 4a and 4b being formed in a small size, the heat insulating members 100, 101, 102 and 103 will not disturb the designing of the jaws 4a and 4b because these members can be formed to be independent from each other.

Examples of the material for the heat insulating members 100, 101, 102 and 103 are resins including ethylene tetrafluoride and ceramics including alumina, but the material is not limited to these as long as it can insulate the heat generated from the heat generating members 47a and 47b from being propagated to the other adjacent parts. Further, the number of heat insulating members, the arrangement thereof, and the dimensions of these are not limited to the above-described one but they may be varied appropriately as long as they can achieve a significant heat insulating effect.

Both of the coaxial cables 50a and 50b are sealed in a single resin tube 105 serving as a fixation member, partially at least in the insertion space 37, and these cables are tied in a bundle to be slidable in the resin tube 105. The coaxial cables 50a and 50b are extended from the heat generating members 47a and 47b through the insertion space 37a, into a channel made in the drive shaft 11 as electricity supply means. In this embodiment, the two coaxial cables 50a and 50b are sealed in the entire insertion space 37a with the resin tube 105. However, it is alternatively possible that the section and/or range of the sealed portions of the coaxial cables 50a and 50b are deformed as long as these cables are fixed.

The distal end portion of the resin tube 105 is situated at the proximal end portion of the first jaw 4a, and it is adhered to each of the first and second insulating members 100 and 101. The outer diameter of the resin tube 105 is made larger than the width of the gap between the first and second heat insulating members 100 and 101, and the resin tube 105 is pushed into the gap when assembling. The proximal end portion of the resin tube 105 is adhered to the distal end portion of the channel formed in the drive shaft 11 within the channel.

The coaxial cables 50a and 50b have an outer diameter smaller than the inner diameter of the resin tube 105. With this structure, if the cables are put through within the fixed resin tube 105, they can be slid to follow the bending movement of the resin tube 105.

With such a structure that the coaxial cables 50a and 50b being inserted to the resin tube 105, a damage to the cable while the apparatus is in use, or the breakage of the cable while the apparatus is being washed, does not easily occur. Further, the cables 50a and 50b are inserted to be slidable, and with this structure, an excessive force does not propagate to the heat generating members 47a and 47b, thus making it possible to prevent a damage to these members 47a and 47b.

In this embodiment, the heat generating means is provided on the first jaw 4a only; however it is alternatively possible that it is provided on the second jaw 4b only, or on both of the first and second jaws 4a and 4b. In compliance with this alternative, the heat insulating members 100, 101, 102 and 103, and the coaxial cables 50a and 50b may be provided on the second jaw 4b only, or on both of the first and second jaws 4a and 4b.

According to this embodiment, a plurality of heat insulating members 100, 101, 102 and 103 are dividedly arranged not only in both sides of the heat generating plate 40, but also in the upper side thereof and between the plate and the coaxial cable 50a. With this structure, it is possible to prevent thermal damages caused to the jaws 4a and 4b and the coaxial cables 50a and 50b while controlling the heat generating plate 40.

Further, a plurality of heat insulating members 100, 101, 102 and 103 are used in accordance with their purposes in this embodiment. More specifically, for example, in a section that requires a high degree of heat insulation, a thick heat insulating member may be employed, whereas in a section of a limited space, a thin heat insulating member may be provided. In this manner, the degree of freedom in designing the heat insulating members can be increased. As a result, it is possible to easily achieve the reduction in the size of the jaws 4a and 4b.

It should be noted here that the fixation member described above should preferably be a single flexible tube in which the electricity supply means can be sealed while at least a part thereof being tied in bundle. With this arrangement, even if the electricity supply means is bent between the insertion portion and the jaws, it will not be entangled with these. Thus, it is possible to achieve an excellent movement of the jaws.

Further, it is preferable that the fixation member should be supported at least partially by a metal pipe. With this structure, the fixation force on the electricity supply means can be further increased, and therefore it is possible to prevent the damage to the heat generating means more effectively.

Figure 12A:
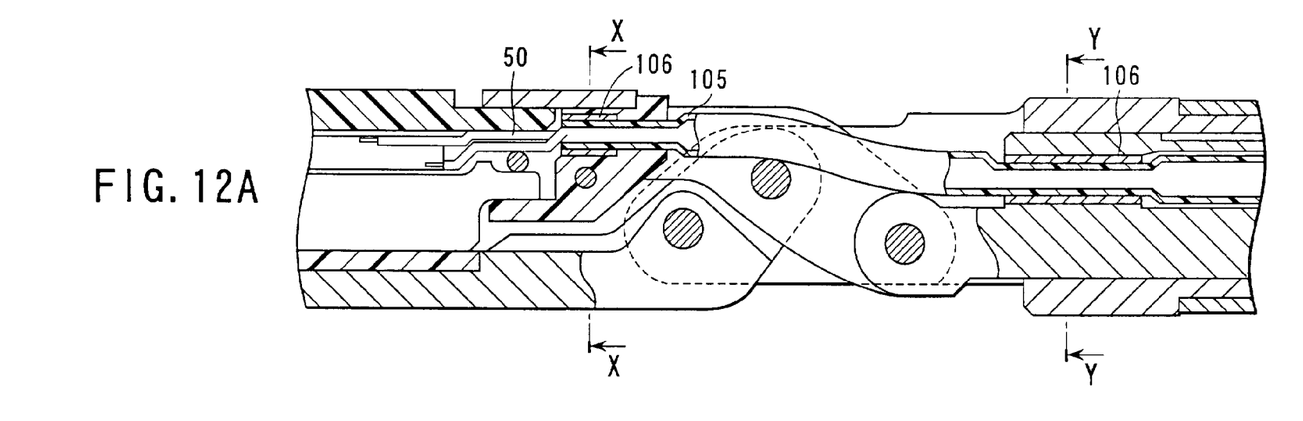
FIG. 12A is a longitudinal section, viewed from side, of a part of the thermal-coagulating cutting forceps according to the sixth embodiment of the present invention.
Figure 12B:
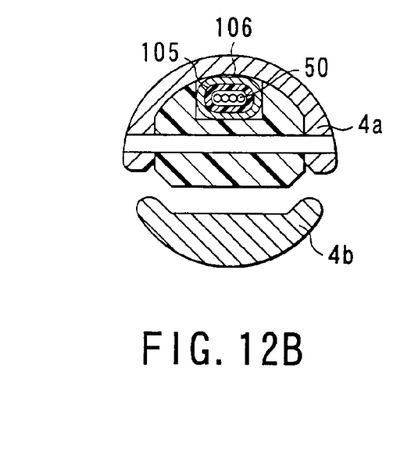
FIG. 12B is a longitudinal section, viewed from top, of the forceps according to the sixth embodiment, taken along the line X—X in FIG. 12A.
Figure 12C:
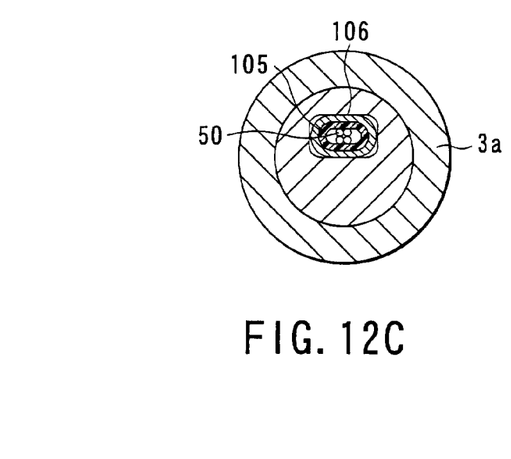
FIG. 12C is a longitudinal section, viewed from top, of the forceps according to the sixth embodiment, taken along the line Y—Y in FIG. 12A.

FIGS. 12A to 12C illustrate a thermal-coagulation and cutting forceps according to the sixth embodiment of the present invention. Here, the same structural elements as those of the fifth embodiment will be designated by the same reference numerals, and the explanations for those elements will not be repeated.

A metal pipe 106 is inserted to each one of the adhered portions of the resin tube 105, that is, between the first heat insulation member 100 situated on the proximal end side of the first jaw 4a and the second heat insulation member 101, and in the distal end side of the channel formed in the drive shaft 11. In the portions where these metal pipes 106 are inserted, the respective portion of the resin tube 105 is reduced in size by the thickness of the metal pipe 106. Further, the resin tube 105 is pierced through the two metal pipes 106. Here, as in the case of the fifth embodiment, the cable that serves as the electricity supply means is sealed in the resin tube 105.

With the above-described structure, the resin tube 105 is fixed by the metal pipes 106. Thus, the fixation force on the cable is more strong as compared to the case where the drive shaft 11 and the resin tube 105 are adhered together.

In this embodiment, a plurality of single-wire cables are employed as the electricity supply means in place of the coaxial cables.

According to this embodiment, the heat insulation member is divided into portions, which are arranged for the respective parts to be thermally insulated. With this structure, it is possible to decrease the thickness of the heat insulation member, and accordingly the size of the jaws can be reduced. Further, with the fixation means for fixing the electricity supply means, a force is not applied to the electricity supply means located within the insertion portion while opening/closing the jaws. Therefore, the heat generating means is not easily damaged, thereby making it possible to improve the durability of the thermal-coagulating and cutting forceps.

According to the present invention, a similar advantage to the above-described one can be achieved not only in the thermal-coagulating and cutting forceps, but also in other therapeutic apparatus that employs heat generating means, such as thermal cutting forceps and thermal coagulating forceps.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A therapeutic device for treating a living tissue, comprising:
   first and second jaws at least one of which is movable to hold the living tissue, the first jaw having an arm portion provided on a proximal side thereof;
   an insertion section configured to support the arm position of the first jaw and the second jaw;
   a member that is heat conductive, the member being attached to the first jaw and having a holding surface which is in contact with the living tissue when the first and second jaws are relatively moved to hold the living tissue;
   the first jaw and the member defining a cavity therebetween;
   an operation section configured to move the first and second jaws;
   at least one heat generating member at least a part of which is provided in the cavity defined between the first jaw and the member, the heat generating member generating heat by electrical energy supplied from a supply of electricity and being thermally coupled with the member without passing electrical current through the living tissue;
   an electricity supply member at least a part of which passes though the arm portion of the first jaw and is electrically connected to the heat generating member to supply electricity to the heat generating member; and
   a damage protecting member configured to protect the electricity supply member from being damaged.

2. The therapeutic device for treating a living tissue, according to claim 1, wherein the damage protecting member has an insulating coating member positioned in at least the first jaw and configured to protect the electricity supply member.

3. The therapeutic device for treating a living tissue, according to claim 2, wherein the insulating coating member has a flexible tube.

4. The therapeutic device for treating a living tissue, according to claim 3, wherein at least a front end portion of the flexible tube is fixed to the jaw.

5. The therapeutic device for treating a living tissue, according to claim 3, wherein the flexible tube is partially inserted in a metal pipe and supported thereby.

6. The therapeutic device for treating a living tissue, according to claim 2, wherein the electricity supply member has a conductive cable covered with the insulating coating member.

7. The therapeutic device for treating a living tissue, according to claim 6, wherein at least a front end portion of the covering material is fixed to the jaw.

8. The therapeutic device for treating a living tissue, according to claim 1, wherein the protection member is a proximal end arm portion of the jaw, configured to cover at least a part of the electricity supply means.

9. The therapeutic device for treating a living tissue, according to claim 8, wherein the proximal end arm portion has a forked shape.

10. The therapeutic device for treating a living tissue, according to claim 1, wherein at least one part of the electricity supply member can be bent.

11. The therapeutic device for treating a living tissue, according to claim 1, wherein the electricity supply member is hard.

12. A therapeutic device for treating a living tissue, comprising:
    holding means for holding the living tissue;
    heat conducting means attached to the holding means and having a holding surface which is contact with the living tissue when the holding means hold the living tissue;
    the holding means and the heat conducting means defining a cavity therebetween;
    insertion means configured to support the holding means;
    operation means configured to allow the holding means to hold the living tissue;
    heat generating means provided in the cavity defined between the holding means and heat
    conducting means and thermally coupled with the heat conducting means in a manner that does not pass electrical current through the living tissue;
    electricity supply means which passes through the holding means and insertion means to supply electricity to the heat generating means; and
    damage protecting means configured to protect the electricity supply means from at least one of mechanical and electrical damages,
    wherein heat generated by the heat generating means is directly transferred to the holding surface through the heat conducting member, and then applied to the living tissue contacted with the holding surface.

* * * * *